US00PP24110P2

(12) United States Plant Patent
Crook

(10) Patent No.: US PP24,110 P2
(45) Date of Patent: Dec. 24, 2013

(54) ***BEGONIA* PLANT NAMED 'BRXBR15-0'**

(50) Latin Name: *Begonia rex cultorum*
Varietal Denomination: BRXBR15-0

(76) Inventor: Gary Crook, Silverton, OR (US)

( * ) Notice: Subject to any disclaimer, the term of this patent is extended or adjusted under 35 U.S.C. 154(b) by 5 days.

(21) Appl. No.: 13/506,599

(22) Filed: Apr. 30, 2012

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Kent L Bell
(74) *Attorney, Agent, or Firm* — Cassandra Bright

(57) ABSTRACT

A new and distinct *Begonia rex cultorum* cultivar named 'BRXBR15-0' is disclosed, characterized by strong, burgundy colored foliage with a very well defined dark purple margin, vigorous year round growth, including the dark winter months. The flexible petioles characteristic of the new variety resist breakage. The new variety is a *Begonia*, and is normally used as an ornamental plant.

1 Drawing Sheet

Latin name of the genus and species: *Begonia rex cultorum.*
Variety denomination: 'BRXBR15-0'.

BACKGROUND OF THE INVENTION

The new cultivar is a product of a planned breeding program. The new variety originated as the result of a crossing performed in 2009 of the unnamed, unpatented, proprietary seed parent variety of *Begonia rex cultorum* with the unnamed, unpatented, proprietary pollen parent, variety of *Begonia rex cultorum*. The new variety was discovered by the inventor, Gary Crook, a citizen of the United States, at a commercial greenhouse in Scotts Mills, Oreg. during 2010, among a planting of seedlings resulting from the previously mentioned crossing.

Asexual reproduction of the new cultivar 'BRXBR15-0' was first performed in Scotts Mills, Oreg. in 2010, by vegetative leaf cuttings. 'BRXBR15-0' has since produced several generations by vegetative leaf cuttings and has shown that the unique features of this cultivar are stable and reproduced true to type.

SUMMARY OF THE INVENTION

The cultivar 'BRXBR15-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BRXBR15-0.' These characteristics in combination distinguish 'BRXBR15-0' as a new and distinct *Begonia rex cultorum* cultivar:

1. Strong burgundy foliage with a very well defined, dark purple margin.
2. Vigorous, year round growth.
3. Unique rapid growth habit at lower temperatures.
4. Flexible petioles, resisting breakage.

PARENT COMPARISON

Plants of the new cultivar 'BRXBR15-0' are similar to plants of the seed parent variety, in most horticultural characteristics. However, plants of the new cultivar 'BRXBR15-0' produce foliage that is brighter in color and larger in size than the foliage of the seed parent. Additionally, plants of the new variety are easier to propagate than plants of the seed parent.

Plants of the new cultivar 'BRXBR15-0' are similar to plants of the pollen parent in most horticultural characteristics. However, plants of the new cultivar 'BRXBR15-0' produce foliage with a more consistent and defined coloration pattern. Additionally, the new variety grows faster than the pollen parent under colder, shorter day conditions.

COMMERCIAL COMPARISON

Plants of the new cultivar 'BRXBR15-0' are similar to plants of the unpatented commercial variety, *Begonia rex cultorum* 'Boston Cherries and Chocolate' in most horticultural characteristics. However, plants of the new cultivar 'BRXBR15-0' produce larger leaves, with a more defined coloration pattern. Additionally plants of 'BRXBR15-0' are faster growing and continue to grow more consistently during the dark winter months than plants of 'Boston Cherries and Chocolate'.

Plants of the new cultivar 'BRXBR15-0' are similar to plants of the unpatented commercial variety, *Begonia rex cultorum* 'Red Rocket' in most horticultural characteristics. However, plants of the new cultivar 'BRXBR15-0' grow faster under winter conditions. Additionally plants of the new variety produce more flexible leaf petioles than 'Red Rocket', and produce foliage with a more consistent and defined coloration pattern.

BRIEF DESCRIPTION OF THE PHOTOGRAPH

The accompanying photograph in FIG. 1 illustrates in full color a typical plant of 'BRXBR15-0' grown in a greenhouse. The pot size is a commercial 6 inch pot. The plant shown is approximately 6 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'BRXBR15-0' plants grown in a commercial controlled greenhouse in Oxnard, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.

Botanical classification: *Begonia rex cultorum* 'BRXBR15-0'.

Age of plant described: Approximately 8 months.

Container size of plant described: 6 inch pot.

PROPAGATION

Type of propagation typically used: Vegetative leaf cuttings.

Time to roots: About 25 days at approximately 20° C.

Root description: Dense and fibrous.

PLANT

Growth habit: Upright growing, outwardly arched fleshy annual.

Pot size of plant described: 6 inch.

Height: Approximately 25 cm.

Plant spread: Approximately 33 cm.

Growth rate: Rapid.

Branching characteristics: Basally emerging foliage, no actual branches, only petioles.

FOLIAGE

*Type*.—Single, basally emerging foliage and long petioles.

*Orientation*.—Outwardly or upwardly facing foliage.

*Strength*.—Very strong, and flexible, resists breakage.

*Texture, top surface*.—Mildly rugulose, mainly non-pubescent. Very infrequent hispidlike hairs, mostly found closer to the margin, approximately 20-30 per mature leaf.

*Texture lower surface*.—Rugose, main surface non-pubescent, veins mildly hispid. Hairs approximately 0.1 cm long, colored near RHS White 155C.

*Appearance*.—Glossy upper surface. Under surface matte.

*Quantity*.—Approximately 15 fully expanded mature leaves and approximately 12 immature leaves.

*Shape of blade*.—Reniform.

*Apex*.—Acute.

*Base*.—Cordate, asymmetrical.

*Margin*.—Dentate, with additional serrations. Less serrate with age.

*Aspect*.—Recurved.

Mature leaves:

*Average length*.—Approximately 13.5 cm.

*Average width*.—Approximately 10 cm.

*Color*.—Mature foliage upper side: Main blade near Greyed-Purple 187B. Margin and veins near petiole attachment, near Greyed-Purple N186A. Mature foliage under side: Near RHS Greyed-Purple N186C.

*Venation*.—Type: Palmate. Venation color upper side: Near RHS Greyed-Purple N186A. Venation color under side: Near RHS Greyed-Purple N186C.

Immature leaves:

*Average length*.—Approximately 10 cm.

*Average width*.—Approximately 6 cm.

*Color*.—Immature foliage upper side: Main blade near RHS Greyed-Purple N186D. Margins and splotch near petiole attachment near RHS Greyed-Purple N186A. Immature foliage under side: A color between Purple N77A and N77B. Margin Purple N77A.

*Venation*.—Type: Palmate. Venation color upper side: Near RHs Greyed-Purple N186D. Venation color under side: Near RHS Greyed-Purple N186C.

PETIOLE

*Length*.—Average Range Approximately 12 to 15 cm.

*Diameter*.—Approximately 0.6 cm.

*Color*.—Near RHS Greyed-Purple N186C.

*Texture*.—Pilose. Hairs range from approximately 0.1 cm to 0.3 cm long, colored near RHS Greyed-Red 181D.

Stipule description:

*Length*.—Approximately 3 cm. Length includes 1 cm awn.

*Diameter*.—Approximately 1.3 cm.

*Apex*.—Aristate.

*Base*.—Truncate.

*Color*.—Near RHS Greyed-Red 181B, upper and lower.

*Texture*.—Upper Surface: Glabrous. Lower Surface: Pilose. Hairs approximately 0.2 cm, colored near RHS Greyed-Red 180B.

FLOWER

Flowering habit: Flowering not observed.

OTHER CHARACTERISTICS

Seeds and fruits: Not Observed.

Disease/pest resistance: Neither resistance nor susceptibility to diseases or pests of *Begonia* has been observed in this variety.

Temperature tolerance: The new variety tolerates temperatures from approximately 0° to 35° C.

What is claimed is:

1. A new and distinct cultivar of *Begonia* plant named 'BRXBR15-0' as herein illustrated and described.

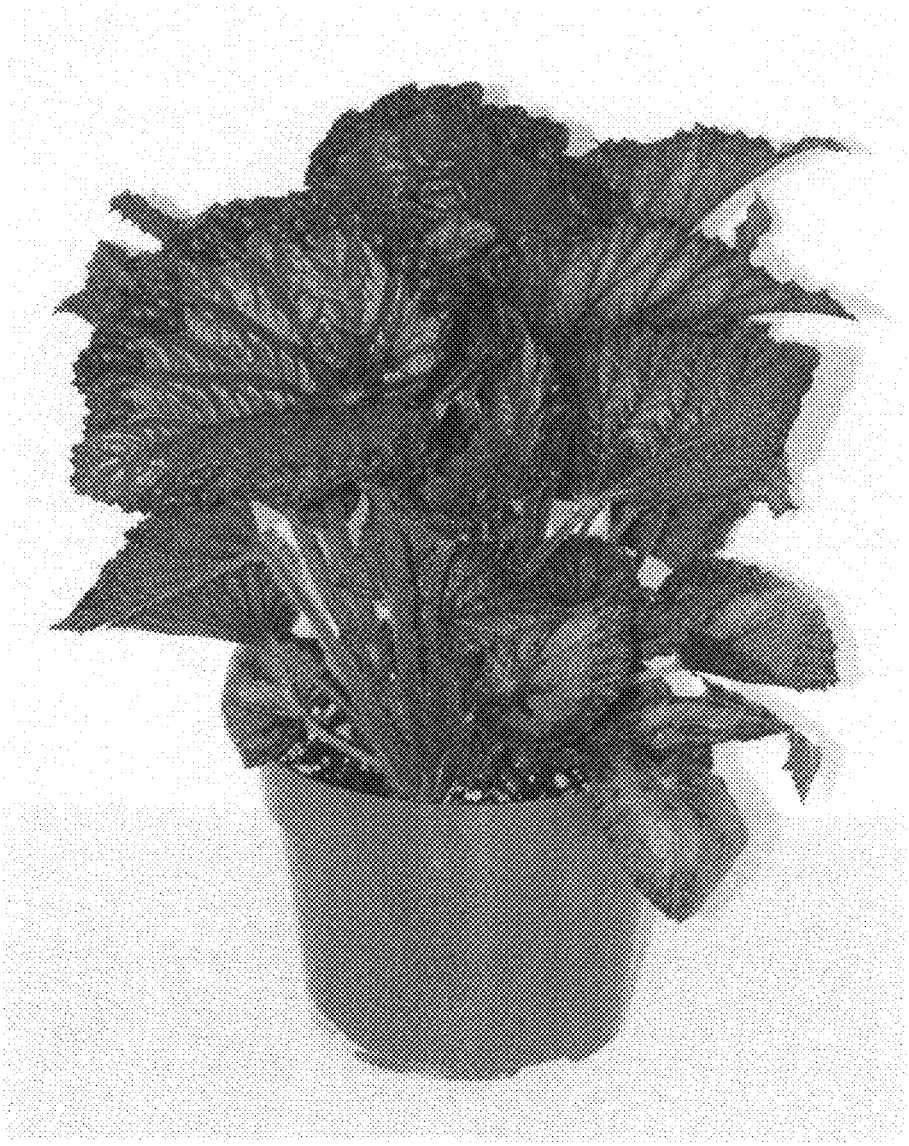

* * * * *